(12) United States Patent
Peterson

(10) Patent No.: US 8,679,133 B2
(45) Date of Patent: Mar. 25, 2014

(54) WOUND DEBRIDEMENT INSTRUMENT

(76) Inventor: Sofia Peterson, Highland, CA (US)

( * ) Notice: Subject to any disclaimer, the term of this patent is extended or adjusted under 35 U.S.C. 154(b) by 150 days.

(21) Appl. No.: 13/086,316

(22) Filed: Apr. 13, 2011

(65) Prior Publication Data

US 2012/0265228 A1 Oct. 18, 2012

(51) Int. Cl.
*A61B 17/32* (2006.01)
(52) U.S. Cl.
USPC .............................. 606/131; 606/170; 606/185
(58) Field of Classification Search
USPC ....................... 30/113.1–113.3, 123.5, 123.7;
433/141–144; 600/562, 564, 567, 570;
606/131, 159–161, 166, 167, 170, 172,
606/180, 184, 185; D24/133, 146, 147, 149
See application file for complete search history.

(56) References Cited

U.S. PATENT DOCUMENTS

| | | | |
|---|---|---|---|
| 4,708,147 A * | 11/1987 | Haaga | 600/566 |
| 5,116,346 A | 5/1992 | Yeh | |
| 5,250,061 A | 10/1993 | Michelson | |
| 5,370,652 A | 12/1994 | Kellan | |
| 5,570,700 A | 11/1996 | Vogeler | |
| 5,586,989 A | 12/1996 | Bray, Jr. | |
| 5,620,455 A | 4/1997 | Grigoletto | |
| 5,827,307 A | 10/1998 | Tipton | |
| 5,836,958 A | 11/1998 | Ralph | |
| 5,968,062 A | 10/1999 | Thomas et al. | |
| 6,270,501 B1 | 8/2001 | Freiberg et al. | |
| 6,398,793 B1 | 6/2002 | McGuire | |
| D470,241 S | 2/2003 | McMichael et al. | |
| 7,708,721 B2 * | 5/2010 | Khaw | 604/264 |
| 2002/0052619 A1 | 5/2002 | Transue | |

OTHER PUBLICATIONS

Rotating Elliptical Biopsy Punch, Inventor: Sam Huot; www.DermalPunch.com, Jan. 11, 2012.
Figure—Volkmann Double Ended Bone Curette, 1 Sheet; www.vitraintl.com/orthopedic-instruments/07.jpg, Jun. 22, 2010.
Figure—Spratt Bone Curette, 1 Sheet, Jun. 22, 2010; www.surgicalsupplyservice.com/images/products/093600L.jpg.

* cited by examiner

*Primary Examiner* — Ryan Severson
(74) *Attorney, Agent, or Firm* — Klein, O'Neill & Singh, LLP

(57) ABSTRACT

A wound debridement instrument for treatment of chronic wounds has an elongate handle with a distal end, a proximal end, and a middle section. An elongate tubular blade body extends distally from the handle distal end and terminates at a distal cutting edge. The tubular body defines a cavity and has a longitudinal axis. The distal cutting edge follows the arc of the tubular body and is angled relative to the longitudinal axis. In some embodiments the tubular body is an incomplete tube, having a longitudinally-extending gap formed therein. Some embodiments may also have a scraping element extending proximally from the handle proximal end.

22 Claims, 11 Drawing Sheets

WOUND DEBRIDEMENT INSTRUMENT

BACKGROUND

1. Field of the Invention

The present disclosure relates to a wound debridement tool for treating chronic wounds.

2. Description of Related Art

Chronic, open wounds such as those that often occur in diabetics typically include at least some unhealthy necrotic tissue that hinders healing. Such dead tissue must be removed in order for the wound to begin healing in earnest. Such wounds typically include curvaceous and irregular edges, and existing straight-bladed instruments such as surgical scalpels are difficult to use in debriding such wounds.

Selective wound debridement of unhealthy wounds such as diabetic ulcers involves removal of devitalized, necrotic necrotic tissue from the ulcer base and edges. Wound debridement generally involves scraping and/or excising tissue from the wound in order to reach healthy, viable tissue. Excisional wound debridement involves cutting through the edges and base of the ulcer into adjacent healthy tissue. Scraping wound debridement involves removing the tissue in layers by scraping the surface of the ulcers. Traditionally, such procedures are performed free hand, using a scalpel or sharp scissors and forceps to lift and cut away the edges. A scalpel or ring curette can be used to scrape the base of the ulcer until the non-viable tissue has been removed and bleeding viable tissue is reached. This process typically requires two or more instruments.

An increase in wound debridement procedures has resulted in an increasing number of primary care physicians practicing wound care in specialized wound healing centers. Usually, these clinicians are not formally trained in free-hand surgical technique and are uncomfortable using a scalpel. While a wound debridement procedure is relatively straightforward, it is difficult for the typical wound care clinician in an outpatient clinic setting to use traditional tools such as a scalpel to make precise incisions around the wound edges to remove non-viable tissue but minimize removal of viable tissue, especially around irregular wound edges. While it is important to remove the required tissue, it is also desirable to remove the minimal amount of adjacent healthy tissue so as to keep the size of the ulcer down and to minimize pain to the patient.

Additionally, conventional reusable curettes are plagued by dulled edges and consequently higher vertical pressure on tissues, which translates to more pain for the patient. Typical ring curettes available on today's markets are scraping tools alone and do not provide the advantage of a cutting and excising device.

SUMMARY

Accordingly, there is a need in the art for a single tool that is simple to use and allows for precise removal of tissue. Preferably the tool would serve to scrape and excise tissue about a chronic wound with an irregular edge. The wound debridement instrument disclosed herein serves to both scrape and excise tissue, which may replace two or more surgical instruments in an excision or debridement surgical procedure.

In accordance with one embodiment, the present invention provides a wound debridement instrument for treating wounds. The instrument comprises an elongate handle having a distal end, a proximal end, and a middle portion between the proximal and distal ends. An elongate tubular blade body extends along a longitudinal axis from the handle distal end and terminates at a blade body distal end. The tubular blade body curves about the longitudinal axis but extends less than 360° about the longitudinal axis so that an elongate gap is defined between first and second blade side edges that extend proximally from the blade body distal end, and a cavity is defined within the tubular blade body. A first point along the blade body distal end is spaced a first longitudinal distance from the handle distal end and a second point along the blade body distal end is spaced a second longitudinal distance from the handle distal end. The first longitudinal distance is greater than the second longitudinal distance so that a plane containing both the first and second points is disposed at an angle less than 90° relative to the longitudinal axis. A sharpened blade edge is defined at the blade body distal end. The blade edge is curved about the longitudinal axis and is defined by the curvature of the tubular blade body. The entire sharpened blade edge lies in the plane that is disposed at an angle less than 90° relative to the longitudinal axis. A scraping element extends proximally from the handle proximal end. The scraping element comprises an elongate scraping edge.

In accordance with another embodiment, the present invention provides a wound debridement instrument for treating wounds. The instrument comprises an elongate handle having a distal end, a proximal end, and a middle portion between the proximal and distal ends. An elongate tubular blade body extends along a longitudinal axis from the handle distal end and terminates at a blade body distal end. The tubular blade body curves about the longitudinal axis, and a cavity is defined within the tubular blade body. A first point along the blade body distal end is disposed longitudinally distal of a second point along the blade body distal end so that a plane containing both the first and second points is disposed at an angle less than 90° relative to the longitudinal axis. A sharpened blade edge is defined at the blade body distal end. The blade edge is curved about the longitudinal axis and is defined by the curvature of the tubular blade body.

In one such embodiment, the entire sharpened blade edge lies in the plane that is disposed at an angle less than 90° relative to the longitudinal axis. In a further embodiment, the plane is disposed at an angle between 30-60° relative to the longitudinal axis. In a still further embodiment, the plane is disposed at an angle about 45° relative to the longitudinal axis.

Another embodiment additionally comprises a third point and a fourth point defined along the blade body distal end, and the blade body distal end is shaped so that the first, second, third and fourth points are incapable of being in the same plane.

In another embodiment, along at least a portion of its length the tubular blade body extends less than 360° around the longitudinal axis so that an elongate gap is defined between first and second blade side edges that extend proximally from the blade body distal end.

In one such embodiment, the elongate gap extends from the blade body distal end to the handle distal end. In another embodiment, the first point is the distal-most point on the blade body distal end and the second point is the proximal-most point on the blade body distal end, and wherein the first blade side edge intersect the blade body distal end at the second point. In a further such embodiment, the first and second points along the blade body distal end are spaced more than 90° from one another. In yet further such embodiment, the first and second points along the blade body distal end are spaced more than 135° from one another.

In still another embodiment, the blade body is selectively attachable to the handle distal end.

In a further embodiment, the tubular blade body has a substantially circular cross-sectional shape. In yet a further embodiment, the tubular blade body has a substantially non-circular, oval cross-sectional shape.

Yet another embodiment additionally comprises a second treatment tool extending proximally from the handle proximal end. In one such embodiment, the second treatment tool comprises a second tubular blade body. In another embodiment, the second treatment tool comprises a scraping element comprising an elongate scraping edge.

In further embodiments, the handle and scraping element are unitarily formed of a first material, and the blade body is formed of a second material that is harder than the first material. In yet further embodiments, the scraping element additionally comprises length measurement indicia configured to measure a longitudinal length from a proximal tip of the scraping element.

Still another embodiment additionally comprises a second treatment tool extending proximally from the handle proximal end, and the second treatment tool comprises a scraping element comprising an elongate scraping edge.

DETAILED DESCRIPTION

Figure 1:
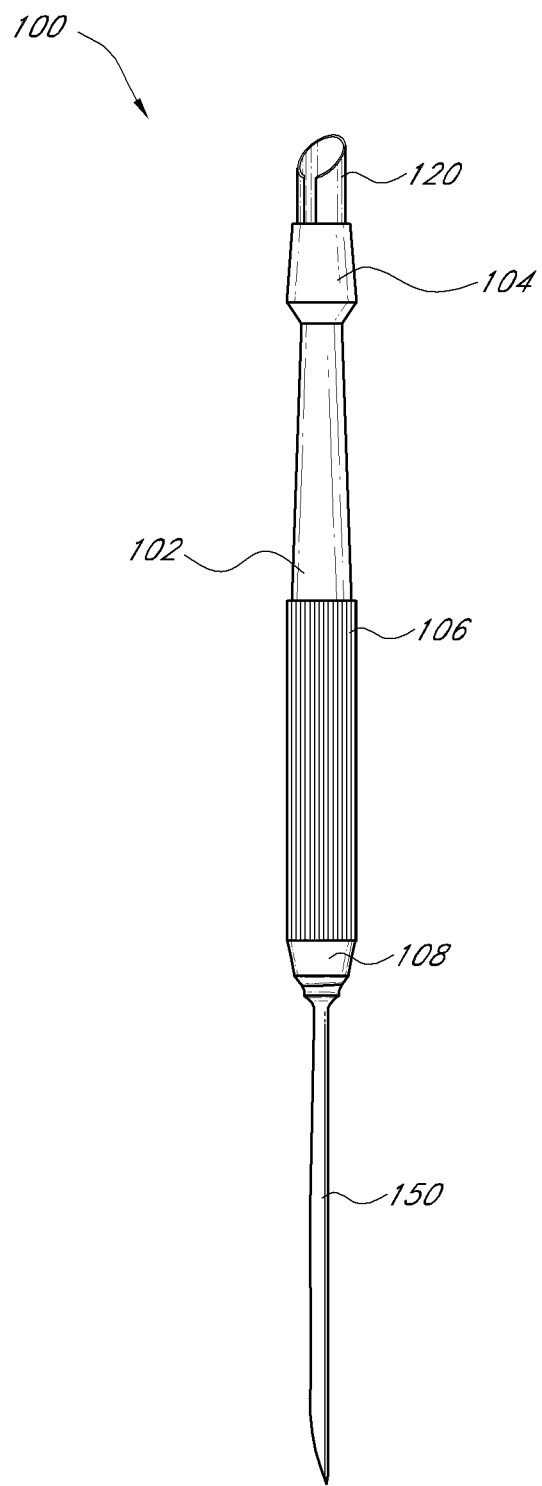
FIG. 1 is a perspective view of one embodiment of a wound debridement instrument.
Figure 2:
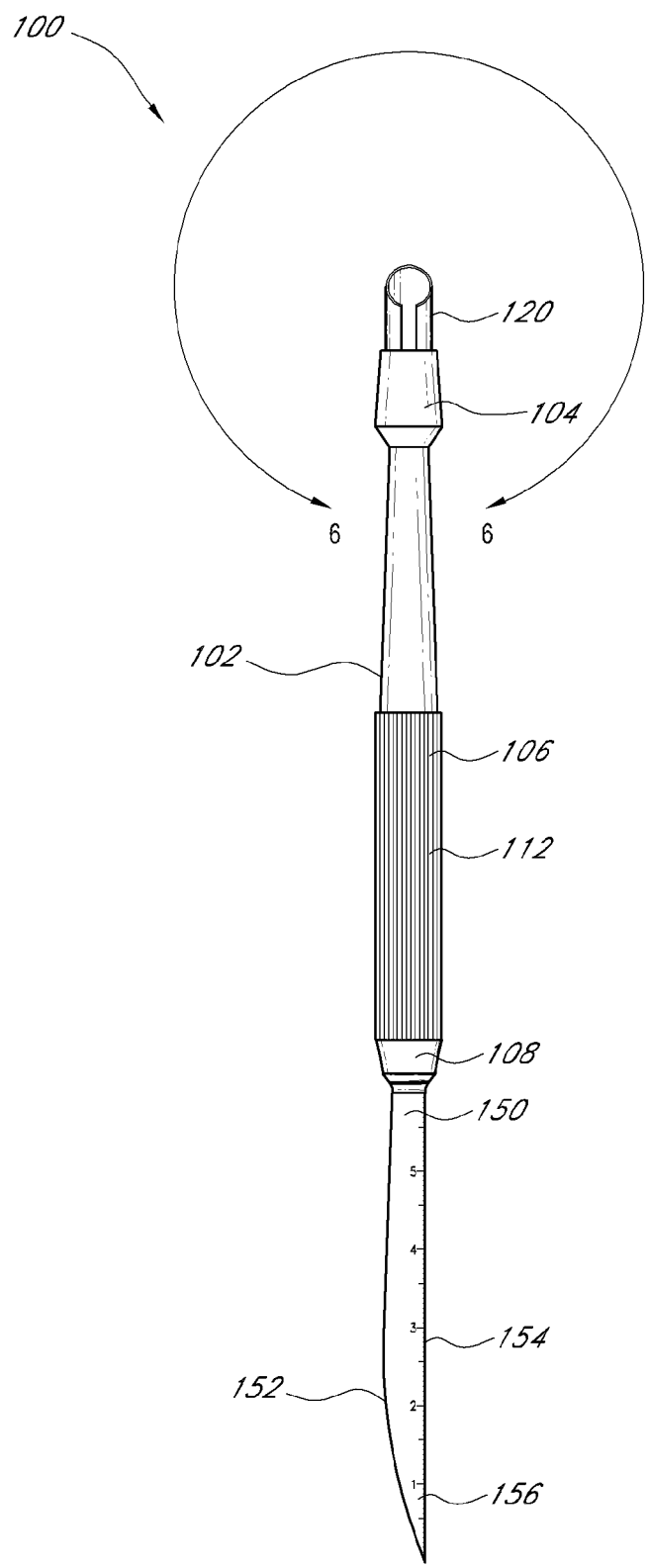
FIG. 2 is a front view of the wound debridement instrument of FIG. 1.
Figure 3:
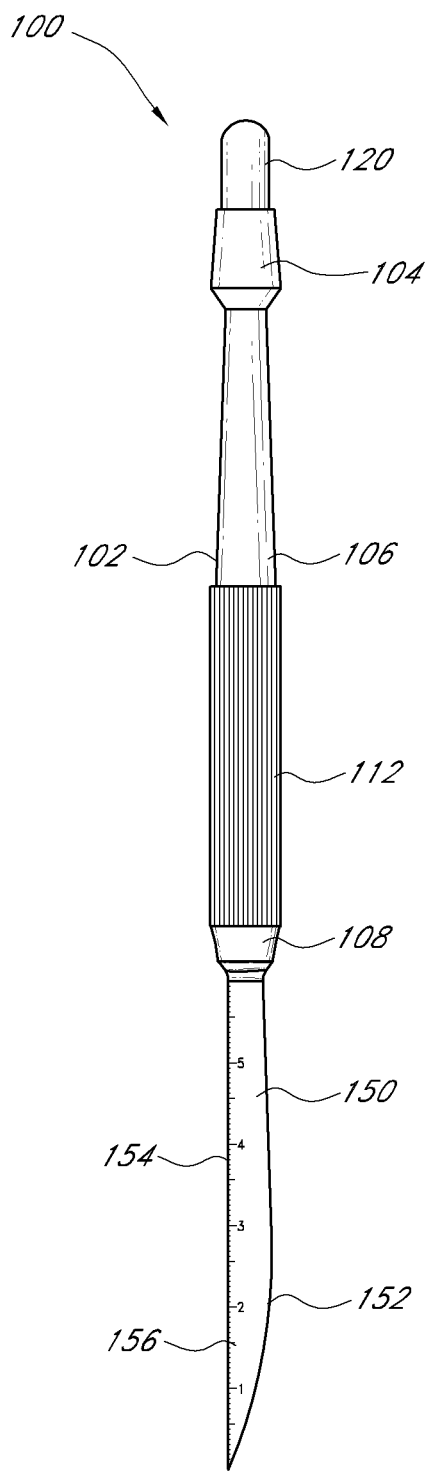
FIG. 3 is a back view of the wound debridement instrument of FIG. 1.

With initial reference to FIGS. 1 through 6, an embodiment of a wound debridement tool is illustrated. The tool comprises an elongate handle 102, a cutting element or first working element 120, and a scraping element or second working element 130. The elongate handle 102 is generally cylindrical in cross-section and comprises a distal end portion 104, a mid-section 106, and a proximal end portion 108. The distal end 104 is coupled to the cutting element 120 and the proximal end is coupled to the scraping element 150.

The mid-section 106 preferably is provided with a textured surface 112 that extends lengthwise along the midsection. Preferably the textured surface 112 is finely grooved or ribbed so as to provide traction on the handle. In some embodiments, the length of the textured surface may vary. For example the textured surface may extend the length of the entire handle, providing the handle with additional traction.

A portion of the mid section 106 preferably tapers inwardly toward the proximal end 108. The proximal end 108 is configured to couple with the scraping element 150. In some embodiments the scraping element 150 may be formed unitarily with the handle. For example, the handle and scraping element may be manufactured as a single piece of material. In other embodiments the scraping element 150 may be releasably coupled to the handle 102.

In the illustrated embodiment, the scraping element comprises a scraping edge 152 and a measuring edge 154. The scraping edge 152 preferably is a curved plastic edge that serves as a scraping device to scrape or clear away tissue. Though sharpened in a preferred embodiment, the plastic edge is blunt relative to a sharpened metal blade. In other embodiments the plastic edge may have different shapes and sizes, and may or may not be sharpened and also, other materials may be employed for the scraping element. The measuring edge 154 preferably is substantially straight and has measurement markings 156 that correspond to a specific measurement standard, such as English or metric. The markings 156 may be etched, molded, printed or applied to the instrument using another method. The markings 154 may be used to accurately measure dimensions such as the depth of the wound treated during a procedure. In the illustrated embodiment, the scraping element comes to a sharp point at its proximal tip. In other embodiments the proximal tip may be blunt.

The handle and scraping element of the tool preferably are made from plastic materials which are suitable for injection molding processes, such as, for example, high impact polystyrene. The handle is designed and molded with features described above to provide a properly balanced tool which allows for maximum control in the hands of the physician. The textured surfaces provide traction and gripping surfaces and reduce the potential for slippage when the tool is actually used. Preferably, the material and design of the handle provide the user with a tool having weight distributed as necessary to properly balance the tool.

A portion of the mid section 106 in the illustrated embodiment tapers inwardly toward the distal end 104, and the diameter of the handle slightly increases or flares out at the distal end 104 to accommodate the cutting element 120. However, it is to be understood that various shapes may be employed for the handle and midsection six in order to facilitate ease of holding and hand comfort during use. The distal end portion 104 preferably terminates in a generally flat end surface or face 114. The distal end portion 104 is configured to accommodate the cutting element and will vary in shape and size depending upon the shape and size of the cutting element 120.

In this embodiment the cutting element is permanently coupled to the end surface 114 of the distal end 104. In other embodiments the cutting element 120 may be mounted or coupled in other configurations. For example, in some embodiments the cutting element 120 may be selectively removable, allowing the cutting element 120 to be replaced with a new or different cutting element. The distal end 104 may also be configured to selectively accommodate a plurality of cutting elements that are different diameters and heights.

It will be appreciated that the handle preferably is of sufficient length so that a clinician can comfortably use one end of the instrument without interference from the tool on the opposite end of the handle, which tool is not currently in use during the procedure. Preferably, when the physician is using the scraping element, the cutting element is oriented such that the cutting element will not cut or slice the physician's skin.

Figure 4:
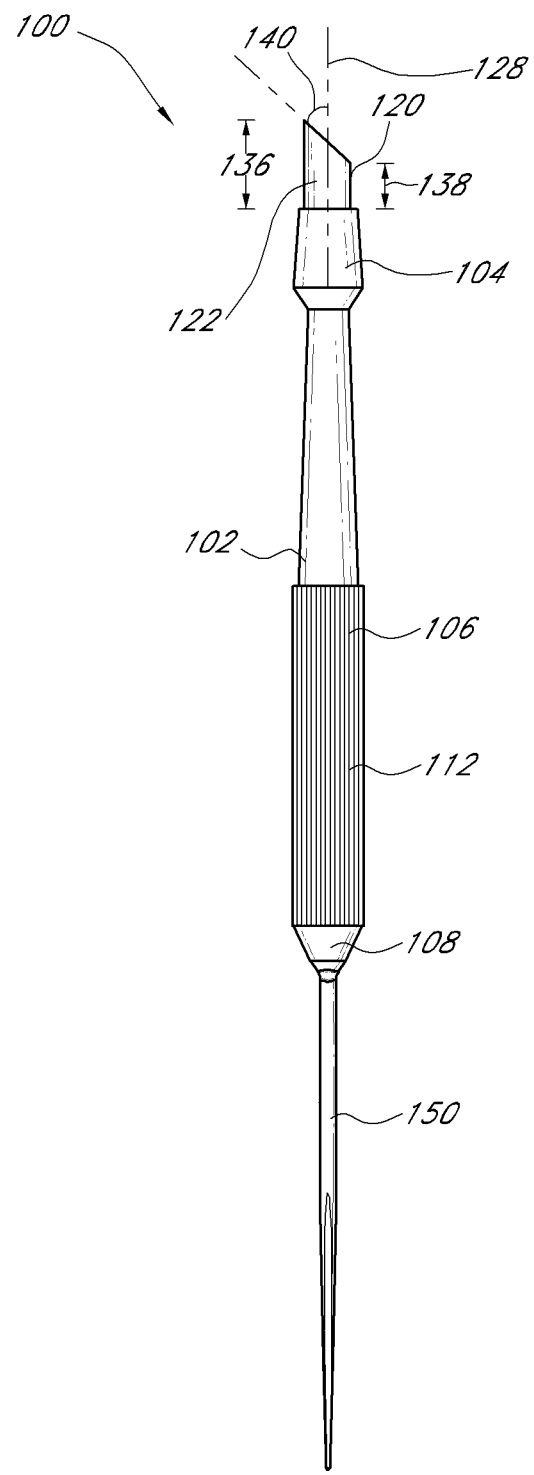
FIG. 4 is a side view of the wound debridement instrument of FIG. 1.
Figure 5:
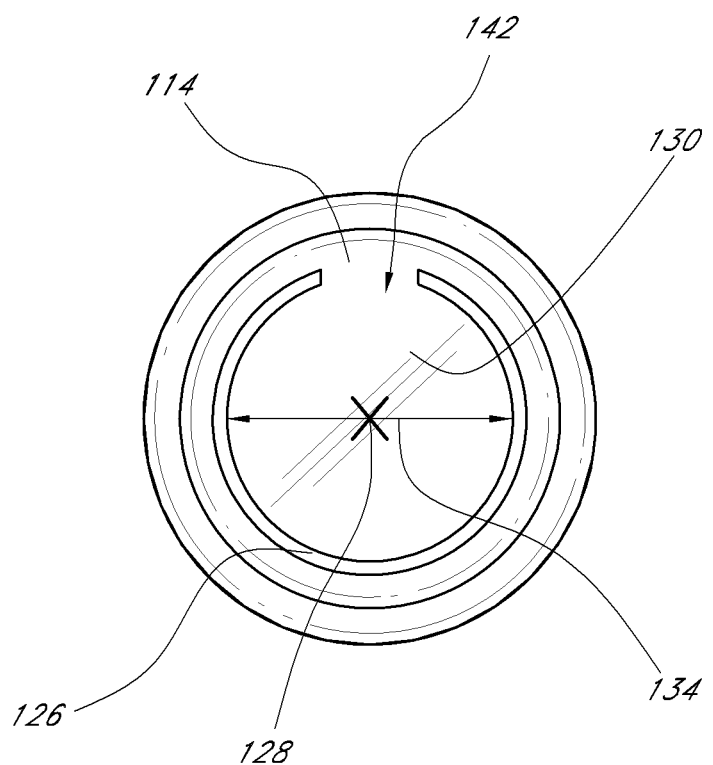
FIG. 5 is an end view of the wound debridement instrument of FIG. 1.
Figure 6:
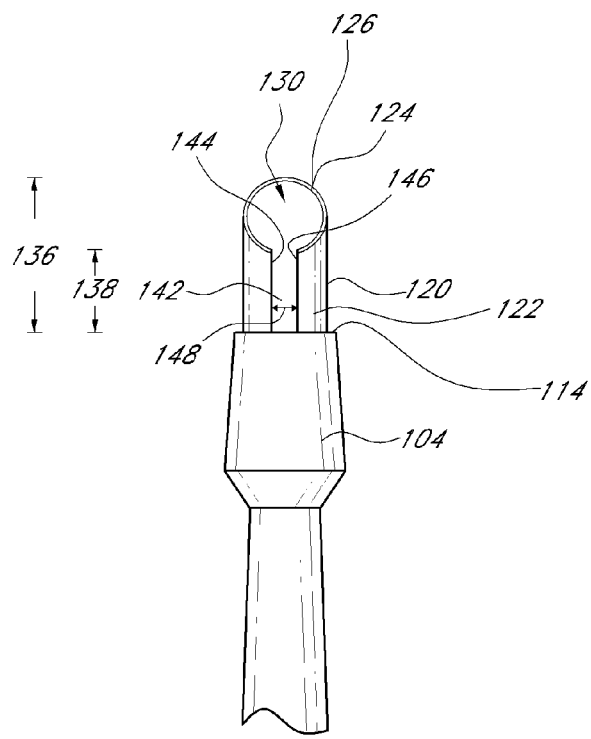
FIG. 6 is an enlarged view taken along line 6-6 of FIG. 2.

With specific reference next to FIGS. 4-6, the cutting element 120 is discussed in more detail. As shown, the cutting element 120 comprises an elongate tubular blade body 122 that extends distally from the handle end surface 114 and terminates in a blade body distal end 124. The tubular blade body 122 curves about a longitudinal axis 128 of the device, and defines a cavity 130 therewithin. A sharp cutting edge 126 is defined at the blade body distal end 124, in that the distal end is sharpened to make the cutting edge.

In the illustrated embodiment, the elongate tubular body 122 is circular in cross-section. In other embodiments the tubular body can have other cross-sectional shapes, such as elliptical or even non-symmetrical shapes. Further, the illustrated tubular blade body 122 has a diameter 134 that is constant along the length of the body. In other embodiments, the diameter may change along the length of the blade body, either increasing or decreasing along the body's length.

Preferably the length of the tubular body 122 varies along the cutting edge 126. For example a maximum length 136 is defined between the handle distal surface 114 and a distal-most point on the cutting edge 126. A minimum length 138 is defined between the handle distal surface 114 and a proximal-most point along the cutting edge. A line taken through the distal-most point and the proximal-most point defines a blade angle 140 relative to the longitudinal axis 128. Preferably the blade angle 140 is less than 90°.

In the illustrated embodiment, the blade angle 140 is about 45°. In other embodiments the blade angle can be any angle within the range of 15°-75°, more preferably within the range of 30°-60°, and even more preferably within the range of 40°-50°. Also in the illustrated embodiment, the entire cutting edge 126 lies in a single plane. In other embodiments, the entire cutting edge may not all lie in a single plane.

With continued reference to FIGS. 5 and 6, preferably the tubular blade body 122 extends less than 360° about the longitudinal axis 128 so that an elongate gap 142 is defined between first and second blade body side edges 144, 146. The blade side edges 144, 146 and gap 142 preferably extend proximally from the blade body distal end 124. In the illustrated embodiment, the gap 142 extends the entire distance between the body distal end and the handle distal surface 114. In other embodiments, the gap may extend only a portion of the distance, and may not disturb the blade body distal end so that the cutting edge 126 is contiguous for 360° about the longitudinal axis 128. Further, in the illustrated embodiment a gap width 148 is uniform along the length of the tubular blade body 122. In other embodiments the gap may vary in width and shape along its length.

Preferably the gap 142 is of sufficient size that a vacuum is not formed within the cavity 130 when the cutting element 126 is used to excise and remove tissue. In the illustrated embodiment, the first and second blade side edges 144, 146 are the same length, so that the intersection of the first blade side edge 144 with the cutting edge 126 is the same distance from the end surface 114 as is the intersection between the second blade side edge 146 and the cutting edge 126. Also, such intersections are both at the minimum length 138 of the cutting element 120. In other embodiments, the blade side edges may have different lengths so that one of such intersections is distal of the other, and/or the intersections described above may be at any point along the cutting edge.

As noted above, the cutting edge 126 preferably comprises the tubular blade body distal end 124 sharpened to a beveled edge. Preferably the beveled cutting edge beveled edge is sharpened to a sharp edge for excising and cutting tissue during surgical procedures. In some embodiments, the cutting edge may be sharpened to a semi-sharp edge.

The cutting element preferably is fabricated from oxidation-resistant, surgical grade metals, such as stainless steel or titanium, using conventional metal fabrication techniques.

During a procedure, the physician moves the cutting element 120 across and through the unhealthy tissue. The physician will apply varying amounts of pressure to the tool depending upon the nature of the wound, the sharpness of the cutting edge 126, and the desired depth required for removal of unhealthy tissue. The circular and angled shape of the cutting edge 126 provides a versatile cutting surface that makes it easier to cut and excise dead tissue along curving, odd-shaped lines, while preserving as much live tissue as possible. Excised tissue is collected in the cavity 130. The gap 142 in the blade generally prevents a vacuum from forming in the cavity 130 when tissue is extracted, which makes it easier to remove tissue from the cavity 130 during the procedure. The cutting and excision process may be repeated multiple times until all of the necrotic tissue is removed.

In addition to cutting tissue, a clinician may also use the scraping element 150 of the tool to scrape or clear away tissue as appropriate. The plastic edge serves as a blunt (relative to a sharpened metal blade) scraping device to scrape or clear away tissue.

The physician will generally measure the dimensions (including death) of the wound before and/or after the procedure is completed. The etched measuring edge 154 of the illustrated embodiment may be used to accurately measure the depth and other dimensions of the treated wound.

Figure 7:
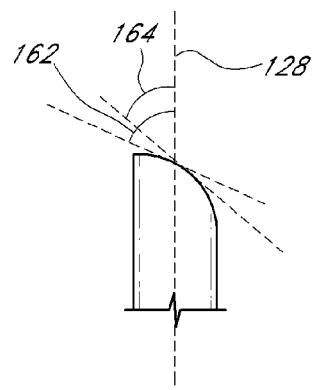
FIG. 7 is a partial view of a cutting element configured in accordance with another embodiment.

In the illustrated embodiment, the entire cutting edge 126 lies in a plane. Other embodiments may employ other shapes so that all points on the cutting edge do not lie in the same plane. For example, with reference next to FIGS. 7 and 8, which show partial side views of additional cutting element embodiments, a first blade angle 162, 162a is defined as an angle between the longitudinal axis 128 and a line through a first pair of points along the cutting edge and at or near the distal-most portion of the cutting edge. A second blade angle 164, 164a is defined as the angle between the longitudinal axis and a line through a second pair of points along the cutting edge but proximal of the first pair of points. In the embodiment illustrated in FIG. 7, the first blade angle 162 is greater than the second blade angle 164, and the blade angle progressively lessens moving proximally along the cutting edge.

Figure 8:
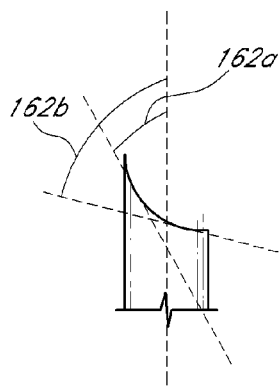
FIG. 8 is a partial view of another cutting element configured in accordance with yet another embodiment.

FIG. 8 presents another cutting edge configuration in which the first blade angle 162a is less than the second blade angle 164a, and the blade angle increases moving proximally along the cutting edge. In still further embodiments, the cutting edge can employ further shapes and curvatures.

Figure 9:
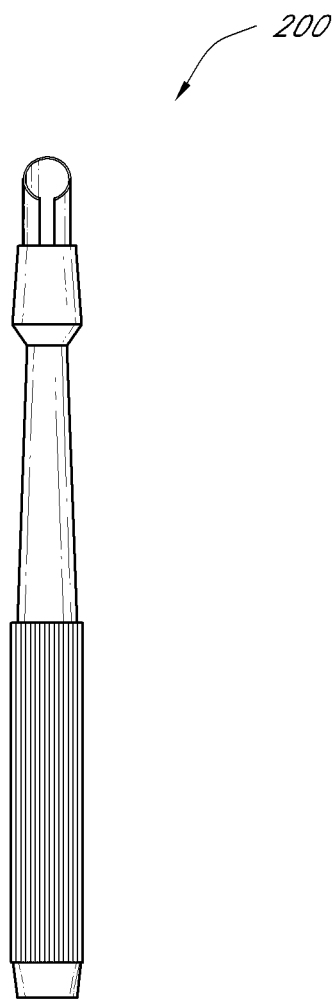
FIG. 9 is a front view of another embodiment of a wound debridement instrument.

With reference now to FIG. 9, another embodiment of a wound debridement instrument is illustrated. The wound debridement instrument shares the same features as the embodiment discussed above in association with FIGS. 1 through 6. In this embodiment the instrument does not have a scraping element coupled to the proximal end.

Figure 10:
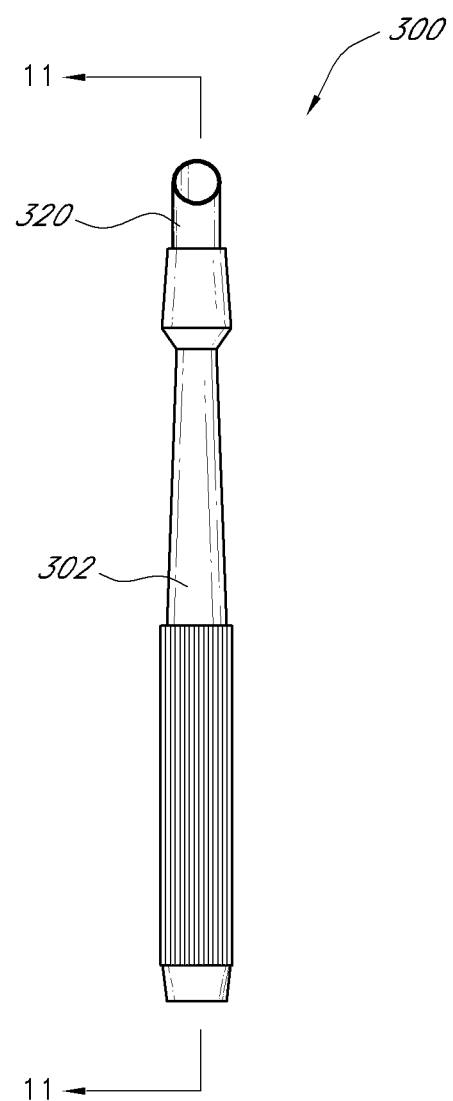
FIG. 10 is a front view of another embodiment of a wound debridement instrument.
Figure 11:
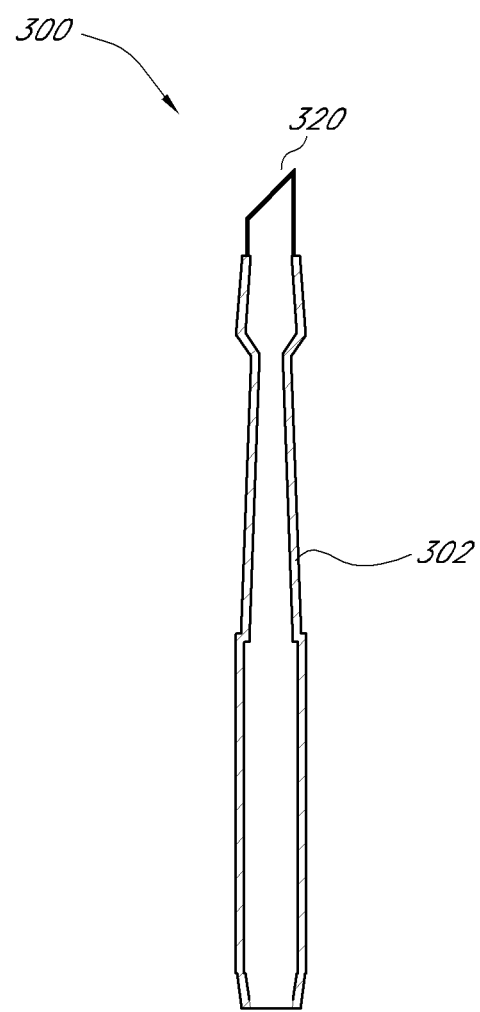
FIG. 11 is a cross section of the wound debridement instrument from FIG. 10 taken along line 11-11.

FIGS. 10 and 11 illustrate another embodiment of the wound debridement instrument in which the wound debridement instrument comprises a cutting element 320 and an elongate handle 302. The elongate handle is generally cylindrical and has proximal, distal, and middle sections. The illustrated handle 302 is hollow and defines an internal cavity 384.

The cutting element 320 is coupled to the distal end of the handle 302. The illustrated cutting element 320 is an angled cylindrical blade that defines a circular cavity 336. The cutting element cavity 336 is contiguous with the handle's internal cavity 384. The size and shape of the cutting element 320 is defined by substantially the same parameters and alternatives as define the cutting element 120 discussed in connection with FIGS. 1 through 6. In this embodiment the cutting element 320 has a contiguous, gap-less blade body 324. In another embodiment, the hollow handle cavity 34 is connected to a source of vacuum configured to clear tissue that may accumulate in the cavities 336, 384.

During the excision and removal of tissue the internal cavity helps to prevent a vacuum from forming, allowing the physician to remove tissue without cleaning out the internal cavity after each excision, and making cleaning the cavity easier. Preferably, this embodiment is disposable, single use, economical, light weight, and provided pre-packaged as a sterile instrument.

Figure 12:
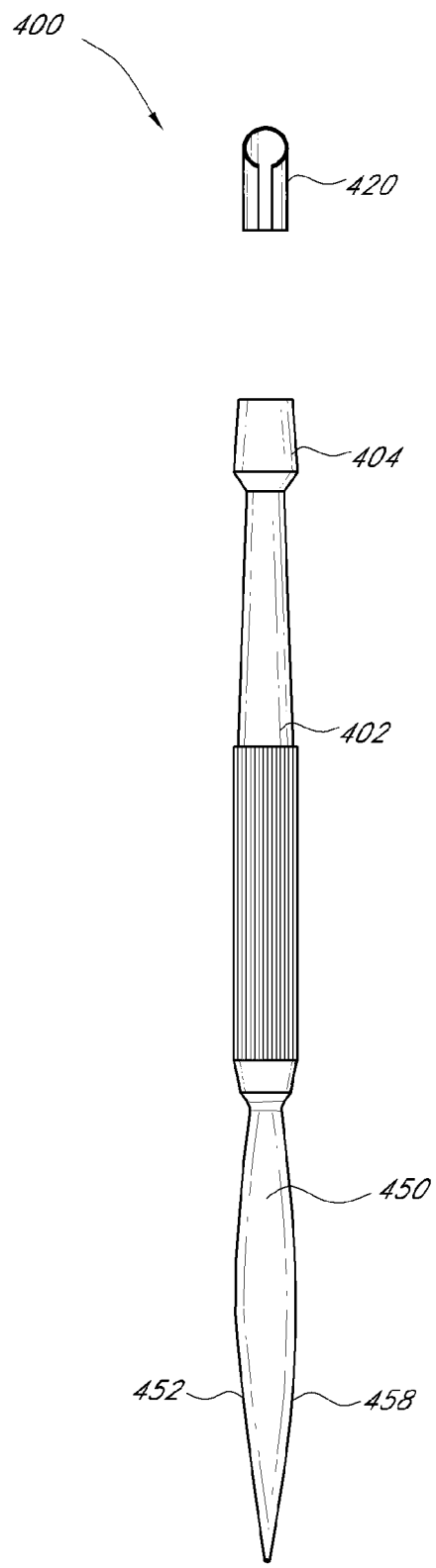
FIG. 12 is an exploded view of another embodiment of a wound debridement instrument.
Figure 13:
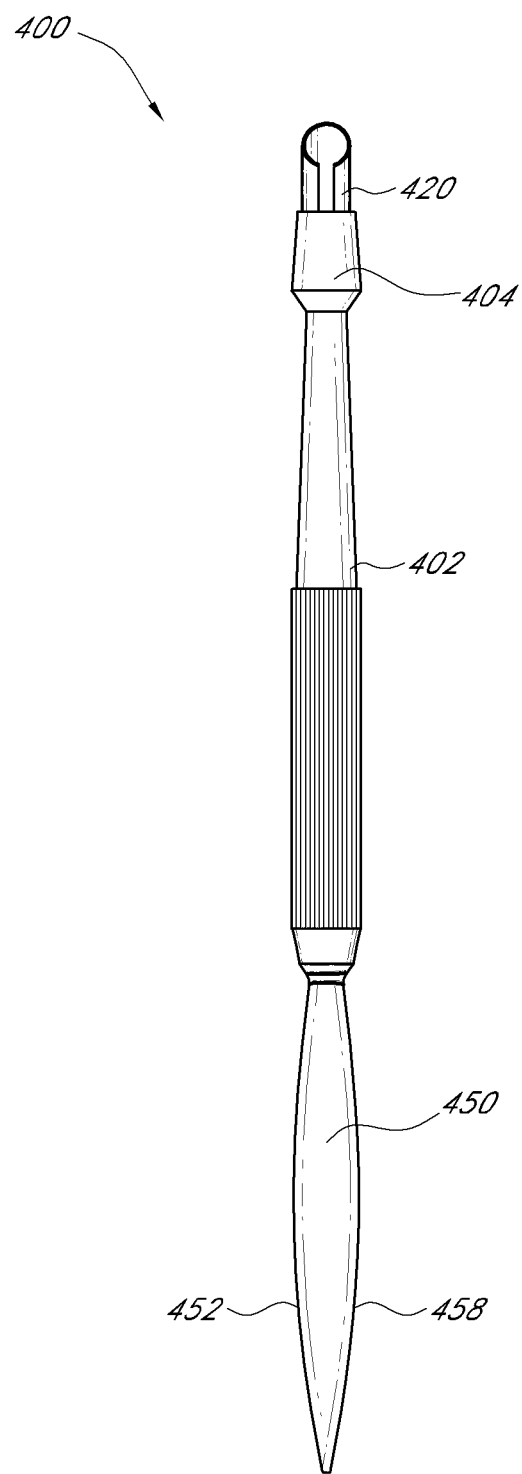
FIG. 13 shows the wound debridement instrument from FIG. 12 fully assembled.

With reference now to FIGS. 12 and 13, another embodiment of a wound debridement instrument is illustrated. The wound debridement instrument comprises a cutting element 420, a handle 402 having proximal, middle, and distal portions, and a scraping element 450. The size and shape of the cutting element 420 preferably is defined by substantially the same parameters an alternative embodiments as define the cutting element 120 discussed in connection with FIGS. 1 through 6. In this embodiment the cutting element 420 is releasably coupled to the distal end of the handle 402. For example, the cutting element 420 fits into an arcuate slot formed in the distal end of the handle. In some embodiments, the handle may be configured to selectively engage any one of a plurality of cutting elements.

In the illustrated instrument the scraping element 450 comprises a first scraping edge 452 and a second scraping edge 458. The first and second scraping edges 452, 458 are different shapes, each edge being configured for a different scraping application or wound shape.

Applicants contemplate that further applications may employ the principles discussed herein in other ways. For example a wound debridement instrument may utilize cutting elements of different sizes on the proximal and distal ends. And it is thus to be understood that the embodiments set forth above are illustrative of inventive principles and features, and these principles may be applied to other surgical procedures that require excisional and scraping tools, such as excising cancerous skin lesions. As such, the principles and features discussed herein can be applied in embodiments of various shapes, sizes and configurations.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, in another embodiment, the handle could be constructed of stainless steel and allow for interchangeable combinations of cutting and scraping elements. It is also contemplated that various combinations or subcombinations of the specific features and aspects of the embodiments may be made and still fall within the scope of the invention. For example, the removable blade illustrated in FIG. 10 can be incorporated into other embodiments. Accordingly, Applicants contemplate that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A wound debridement instrument for treating wounds, comprising:
    an elongate handle having a distal end, a proximal end, and a middle portion between the proximal and distal ends;
    an elongate tubular blade body extending along a longitudinal axis from the handle distal end and terminating at a blade body distal end, the tubular blade body curving about the longitudinal axis but extending less than 360° about the longitudinal axis so that an elongate gap is defined between first and second blade side edges that extend proximally from the blade body distal end, and a cavity is defined within the tubular blade body;
    a first point along the blade body distal end being spaced a first longitudinal distance from the handle distal end and a second point along the blade body distal end being spaced a second longitudinal distance from the handle distal end, the first longitudinal distance being greater than the second longitudinal distance so that a plane containing both the first and second points is disposed at an angle less than 90° relative to the longitudinal axis;
    a sharpened blade edge defined at the blade body distal end, the blade edge being curved about the longitudinal axis and defined by the curvature of the tubular blade body, the entire sharpened blade edge lying in the plane that is disposed at an angle less than 90° relative to the longitudinal axis; and
    a scraping element extending proximally from the handle proximal end, the scraping element comprising an elongate scraping edge.

2. A wound debridement instrument for treating wounds, comprising:
    an elongate, rigid handle having a distal end, a proximal end, and a middle portion between the proximal and distal ends, the handle being made of a first material and having a length along a longitudinal axis;
    an elongate tubular blade body extending along the longitudinal axis from the handle distal end and terminating at a blade body distal end, a length of the blade being less than the handle length, the tubular blade body curving about the longitudinal axis and being made of a second material that is harder than the first material, and a cavity is defined within the tubular blade body, a first point along the blade body distal end being disposed longitudinally distal of a second point along the blade body distal end so that a plane containing both the first and second points is disposed at an angle less than 90° relative to the longitudinal axis; and
    a sharpened blade edge defined at the blade body distal end, the blade edge being curved about the longitudinal axis and defined by the curvature of the tubular blade body.

3. The wound debridement instrument of claim 2, wherein the sharpened blade edge comprises the entire blade body distal end, and a third point and a fourth point are defined along the blade body distal end, wherein the blade body distal end is shaped so that the first, second, third and fourth points are incapable of being in the same plane.

4. The wound debridement instrument of claim 2, wherein along at least a portion of its length the tubular blade body extends less than 360° around the longitudinal axis so that an elongate gap is defined between first and second blade side edges that extend proximally from the blade body distal end.

5. The wound debridement instrument of claim 4, wherein the elongate gap extends from the blade body distal end to the handle distal end and terminates at the handle distal end.

6. The wound debridement instrument of claim 4, wherein the first point is the distal-most point on the blade body distal end and the second point is the proximal-most point on the blade body distal end, wherein the first blade side edge intersects the blade body distal end at the second point, and wherein entire sharpened blade edge is on the blade body distal end and defines a cutting edge so that the first and second blade side edges are not part of the cutting edge.

7. The wound debridement instrument of claim 6, wherein the first and second points along the blade body distal end are spaced more than 135° from one another.

8. The wound debridement instrument of claim 4 additionally comprising a second treatment tool extending proximally from the handle proximal end, wherein the second treatment tool comprises a scraping element comprising an elongate scraping edge.

9. The wound debridement instrument of claim 2, wherein the blade body is selectively attachable to the handle distal end.

10. The wound debridement instrument of claim 2, wherein the tubular blade body has a substantially circular cross-sectional shape.

11. The wound debridement instrument of claim 2, wherein the tubular blade body has a substantially non-circular, oval cross-sectional shape.

12. The wound debridement instrument of claim 2, wherein the blade body distal end extends a contiguous 360° about the longitudinal axis.

13. The wound debridement instrument of claim 12, wherein the blade body comprises a gap formed therethrough and spaced proximally from the blade body distal end.

14. The wound debridement instrument of claim 2, wherein the handle distal end has a diameter greater than a diameter of the tubular blade body.

15. The wound debridement instrument of claim 14, wherein the handle distal end comprises a wall, and the cavity is defined within the tubular blade body and distal of the wall.

16. The wound debridement instrument of claim 2, wherein an outer diameter of the elongate handle changes along its length.

17. The wound debridement instrument of claim 2, wherein the handle comprises a textured outer surface.

18. A wound debridement instrument for treating wounds, comprising:
   an elongate handle having a distal end, a proximal end, and a middle portion between the proximal and distal ends;
   an elongate tubular blade body extending along a longitudinal axis from the handle distal end and terminating at a blade body distal end, the tubular blade body curving about the longitudinal axis, and a cavity is defined within the tubular blade body, a first point along the blade body distal end being disposed longitudinally distal of a second point along the blade body distal end so that a plane containing both the first and second points is disposed at an angle less than 90° relative to the longitudinal axis;
   a sharpened blade edge defined at the blade body distal end, the blade edge being curved about the longitudinal axis and defined by the curvature of the tubular blade body; and
   a second treatment tool extending proximally from the handle proximal end.

19. The wound debridement instrument of claim 18, wherein the second treatment tool comprises a second tubular blade body.

20. The wound debridement instrument of claim 18, wherein the second treatment tool comprises a scraping element comprising an elongate scraping edge.

21. The wound debridement instrument of claim 20, wherein the handle and scraping element are unitarily formed of a first material, and the blade body is formed of a second material that is harder than the first material.

22. The wound debridement instrument of claim 20, wherein the scraping element additionally comprises length measurement indicia configured to measure a longitudinal length from a proximal tip of the scraping element.

* * * * *